(12) United States Patent
Amarasinghe et al.

(10) Patent No.: US 10,639,445 B2
(45) Date of Patent: May 5, 2020

(54) HEADGEAR ASSEMBLY FOR A RESPIRATORY MASK ASSEMBLY

(71) Applicant: ResMed Pty Ltd, Bella Vista, New South Wales (AU)

(72) Inventors: Amal Shirley Amarasinghe, Sydney (AU); Perry David Lithgow, Sydney (AU); Memduh Guney, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 908 days.

(21) Appl. No.: 14/886,207

(22) Filed: Oct. 19, 2015

(65) Prior Publication Data

US 2016/0038708 A1  Feb. 11, 2016

Related U.S. Application Data

(63) Continuation of application No. 13/865,496, filed on Apr. 18, 2013, now Pat. No. 9,168,349, which is a
(Continued)

(51) Int. Cl.
*A61M 16/06* (2006.01)

(52) U.S. Cl.
CPC .... *A61M 16/0683* (2013.01); *A61M 16/0633* (2014.02); *A61M 16/0666* (2013.01)

(58) Field of Classification Search
CPC .............. A61M 16/06; A61M 16/0605; A61M 16/0616; A61M 16/0633; A61M 16/0683;
(Continued)

(56) References Cited

U.S. PATENT DOCUMENTS 1,706,601 A * 3/1929 Drager ................. A62B 18/084
128/207.11
RE20,211 E 12/1936 Motsinger
(Continued)

FOREIGN PATENT DOCUMENTS

DE           29723101 U1    7/1998
DE        199 62 515 A1   12/1999
(Continued)

OTHER PUBLICATIONS

Decision on Rejection issued in related Japanese Application No. 2014-046007 dated Aug. 17, 2015 with English translation (8 pages).
(Continued)

*Primary Examiner* — Tu A Vo
(74) *Attorney, Agent, or Firm* — Nixon & Vanderhye P.C.

(57) ABSTRACT

A respiratory mask assembly for delivering breathable gas to a patient includes a frame and a headgear assembly removably attachable to the frame. The headgear assembly includes a pair of side portions and a rear portion that interconnects the pair of side portions. The pair of side portions includes at least one strap. The rear portion has at least one strap constructed of at least two layers of material. One of the layers of material has a more rigid construction than the other of the layers of material to resist compression of the at least one strap of the rear portion in a first direction which resists movement of the at least one strap of the pair of side straps in the first direction.

29 Claims, 16 Drawing Sheets

Related U.S. Application Data continuation of application No. 13/200,947, filed on Oct. 5, 2011, now Pat. No. 8,443,805, which is a continuation of application No. 12/285,445, filed on Oct. 6, 2008, now Pat. No. 8,042,543, which is a continuation of application No. 10/655,602, filed on Sep. 5, 2003, now Pat. No. 7,509,958.

(60) Provisional application No. 60/424,694, filed on Nov. 8, 2002.

(58) Field of Classification Search
CPC . A61M 16/0688; A61M 16/0694; A61F 5/56; A61F 9/02; A61F 9/027
See application file for complete search history.

(56) References Cited

U.S. PATENT DOCUMENTS

| | | | |
|---|---|---|---|
| 2,353,643 A * | 7/1944 | Bulbulian | A62B 18/084 128/207.11 |
| 2,931,356 A * | 4/1960 | Schwarz | A61M 16/06 128/206.24 |
| 3,234,939 A * | 2/1966 | Morton, Jr. | A62B 18/084 128/206.27 |
| 3,234,940 A * | 2/1966 | Morton, Jr. | A62B 18/084 128/206.27 |
| 3,457,564 A * | 7/1969 | Holloway | A42B 3/14 128/207.11 |
| 3,599,635 A * | 8/1971 | Ansite | A62B 18/084 128/206.28 |
| 4,099,524 A | 7/1978 | Cueman et al. | |
| 4,367,735 A | 1/1983 | Dali | |
| 4,437,462 A | 3/1984 | Piljay et al. | |
| 4,593,688 A | 6/1986 | Payton | |
| 4,640,269 A | 2/1987 | Goins | |
| 5,117,819 A | 6/1992 | Servidio et al. | |
| D334,633 S | 4/1993 | Rudolph | |
| 5,233,978 A | 8/1993 | Callaway | |
| 5,284,469 A | 2/1994 | Jasen et al. | |
| 5,394,568 A | 3/1995 | Brostrom et al. | |
| 5,481,763 A | 1/1996 | Brostrom et al. | |
| 5,488,948 A | 2/1996 | Dubruille et al. | |
| 5,490,504 A | 2/1996 | Vrona et al. | |
| 5,517,986 A | 5/1996 | Starr et al. | |
| 5,529,062 A | 6/1996 | Byrd et al. | |
| 5,542,128 A | 8/1996 | Lomas et al. | |
| D383,204 S | 9/1997 | Lomas | |
| 5,771,886 A | 6/1998 | Maire et al. | |
| 5,806,516 A | 9/1998 | Beattie | |
| 5,840,050 A | 11/1998 | Lerman | |
| 5,921,239 A | 7/1999 | McCall et al. | |
| 5,924,421 A | 7/1999 | Rosbrook et al. | |
| 5,950,248 A | 9/1999 | Kawashima et al. | |
| 5,975,079 A | 11/1999 | Hellings et al. | |
| 6,016,807 A | 1/2000 | Lodge | |
| 6,019,101 A * | 2/2000 | Cotner | A61M 16/06 128/206.18 |
| 6,062,222 A | 5/2000 | Lewis et al. | |
| 6,105,573 A | 8/2000 | Delaplane et al. | |
| 6,119,693 A | 9/2000 | Kwok et al. | |
| D433,127 S | 10/2000 | Gazzara | |
| 6,269,814 B1 | 8/2001 | Blaszczykiewicz et al. | |
| 6,338,342 B1 | 1/2002 | Fecteau et al. | |
| 6,374,826 B1 | 4/2002 | Gunaratnam et al. | |
| 6,422,238 B1 | 7/2002 | Lithgow | |
| 6,467,483 B1 | 10/2002 | Kopacko et al. | |
| 6,470,886 B1 * | 10/2002 | Jestrabek-Hart | A61M 16/0683 128/207.11 |
| 6,494,207 B1 | 12/2002 | Kwok | |
| 6,591,837 B1 | 7/2003 | Byram | |
| D485,905 S | 1/2004 | Moore | |
| 6,732,733 B1 | 5/2004 | Brostrom et al. | |
| 6,772,760 B2 | 8/2004 | Frater et al. | |
| 6,805,117 B1 | 10/2004 | Ho et al. | |
| 6,907,882 B2 | 6/2005 | Ging | |
| 7,188,620 B2 | 3/2007 | Amarasinghe | |
| 7,204,250 B1 | 4/2007 | Burton | |
| 7,219,669 B1 | 5/2007 | Lovell et al. | |
| 7,509,958 B2 | 3/2009 | Amarasinghe et al. | |
| 7,802,573 B2 | 9/2010 | Amarasinghe | |
| 8,042,543 B2 | 10/2011 | Amarasinghe et al. | |
| 2002/0096173 A1* | 7/2002 | Berthon-Jones | A61M 16/00 128/204.23 |
| 2002/0096176 A1 | 7/2002 | Gunaratnam et al. | |
| 2002/0117177 A1 | 8/2002 | Kwok | |
| 2003/0005509 A1 | 1/2003 | Kelzer | |
| 2003/0051732 A1 | 3/2003 | Smith et al. | |
| 2003/0196657 A1 | 10/2003 | Ging et al. | |
| 2004/0067333 A1 | 4/2004 | Amarasinghe | |
| 2004/0083534 A1* | 5/2004 | Ruiz | A61F 5/56 2/171.2 |
| 2004/0112377 A1 | 6/2004 | Amarasinghe et al. | |
| 2007/0169777 A1 | 7/2007 | Amarasinghe | |
| 2009/0038622 A1 | 2/2009 | Amarasinghe et al. | |
| 2010/0319688 A1 | 12/2010 | Amarasinghe | |
| 2012/0024290 A1 | 2/2012 | Amarasinghe et al. | |
| 2012/0024729 A1 | 2/2012 | Dietenberger | |
| 2013/0233320 A1 | 9/2013 | Amarasinghe et al. | |

FOREIGN PATENT DOCUMENTS

| | | |
|---|---|---|
| DE | 19947722 | 4/2001 |
| EP | 0747078 A2 | 12/1996 |
| EP | 1 020 201 | 7/2000 |
| EP | 1 020 201 A2 | 7/2000 |
| EP | 1 189 650 A1 | 3/2002 |
| EP | 2298410 | 3/2011 |
| FR | 2 618 340 A | 1/1989 |
| GB | 2 247 396 A | 3/1992 |
| JP | 62-09460 | 1/1987 |
| JP | 8-57055 | 3/1996 |
| JP | 2000-254229 | 9/2000 |
| JP | 3076462 | 1/2001 |
| JP | 2001-505080 | 4/2001 |
| JP | 2002-537078 | 11/2002 |
| JP | 2004-522481 | 7/2004 |
| JP | 2000-102624 | 4/2011 |
| JP | 52-36897 | 7/2013 |
| JP | 2016-34593 | 3/2016 |
| WO | WO 96/25983 | 8/1996 |
| WO | 96/28207 | 9/1996 |
| WO | WO 97/20597 | 6/1997 |
| WO | 98/13103 | 4/1998 |
| WO | WO 98/48878 A2 | 11/1998 |
| WO | WO 00/50122 | 8/2000 |
| WO | WO 02/07806 A1 | 1/2002 |
| WO | 0245784 | 6/2002 |
| WO | WO 02/47749 A1 | 6/2002 |
| WO | WO 02/47763 A1 | 6/2002 |

OTHER PUBLICATIONS

European Communication with extended European Search Report issued in Application No. 14198923.6, dated Apr. 8, 2015, (5 pages).
Decision of the Assistant Commissioner for NZ Application No. 585295 dated Feb. 5, 2015, 30 pages.
European Examination Report for European Application No. 03 810 330.5-1651 dated Jan. 28, 2015, 4 pages.
First Office Action issued in corresponding Japanese Application No. 2014-046007 with English translation (9 pages).
First Amended Counterstatement in corresponding New Zealand Patent Application No. 585295, dated Feb. 14, 2013, 12 pages.
Statutory Declaration of Dr. Glenn Millman Richards in Support of New Zealand Patent Application No. 585295 in corresponding New Zealand Patent Application No. 585295, dated Dec. 9, 2013, 14 pages.
Statutory Declaration of Gregory James Olsen in corresponding New Zealand Patent Application No. 585295, dated Sep. 5, 2013, 7 pages.

(56) References Cited

OTHER PUBLICATIONS

European Search Report for Application No. 12190811.5-1651/2591818, dated Feb. 12, 2013 (5 pages).
European Search Report for Application No. 12190819.8-1651/2583712, dated Feb. 12, 2013 (6 pages).
Japanese Office Action, "Notice of Reasons for Rejection", dated Sep. 4, 2013 for Application No. 2012-238713, with English translation, (7 pages total).
First Office Action for co-pending Chinese Application No. 201010185131.3, dated Nov. 11, 2010, 9 pages.
Japanese Office Action and English translation for copending Japanese Application No. 2004-548920, dated Mar. 16, 2010, 8 pages.
Office Action from co-pending European Application No. 03810330.5, dated Oct. 21, 2010, 6 pages.
PCT International Search Report for PCT/AU03/01161, dated Oct. 14, 2003.
Supplementary Search Report for co-pending European Application No. 03810330.5, dated Jun. 25, 2010, 3 pages.
U.S. Appl. No. 10/390,681, filed Mar. 19, 2003.
U.S. Appl. No. 29/166,190, filed Aug. 9, 2002.
U.S. Appl. No. 60/377,254, filed May 3, 2002.
U.S. Appl. No. 60/397,195, filed Jul. 22, 2002.
U.S. Appl. No. 60/402,509, filed Aug. 12, 2002.
Examination Report for corresponding New Zealand Application No. 595935, dated Oct. 28, 2011, 2 pages.
Letter to New Zealand Patent Office with Notice of Opposition and Extension Letter for corresponding New Zealand Patent Application No. 585295, dated Apr. 23, 2012, 4 pages.
Notice of Opposition for corresponding New Zealand Patent Application No. 585295, dated May 30, 2012, 22 pages.
Notice of Reasons for Rejection and English Translation for corresponding Japanese Application No. 2010-205442, dated Jun. 19, 2012, 7 pages.
Supplementary European Search Report for EP 01270356.7 dated Feb. 3, 2006, 3 pages.
European Office Action for corresponding EP Application No. 01 270 356.7, dated Jun. 11, 2007, 3 pages.
Extended European Search Report in EP 10 18 5039 dated Feb. 16, 2011.
New Zealand Examination Report for Patent Application No. 602732 dated Oct. 4, 2012, 2 pages.
European Patent Office Communication for corresponding EP Application No. 03 810 330.5-1257, dated Sep. 28, 2012, 4 pages.
Extended European Search Report in EP 10 18 5034 dated Feb. 22, 2011, 6 pages.
European Search Report for corresponding EP Appln. No. 10183627, dated Mar. 1, 2011, 12 pages.

First Examination Report issued in related New Zealand Application No. 731635, dated May 18, 2017, 1 page.
Second Office Action issued in related Japanese Application No. 2015-246225, with English translation dated Jun. 5, 2017, 10 pages.
First Office Action issued in related Japanese Application No. 2016-240978 dated Sep. 25, 2017, with English translation, (21 pages).
Further Examination Report issued in related New Zealand Application No. 622333 dated Dec. 8, 2015, 2 pages.
ResMed Standard Mask and Horizontal Headgear Photos, first sold Sep. 1988, 6 pages.
ResMed Standard Mask and Triangular Headgear Photos, first sold Sep. 1988, 6 pages.
MAP Silent Papillon Headgear Photos, first sold Apr. 2002, 6 pages.
First Office Action issued in related European Application No. 12 190 819.8 dated Oct. 17, 2017, (3 pages).
Statement of Case issued in related New Zealand Application No. 729130, dated Nov. 23, 2017, (29 pages).
First Amended Notice of Opposition in related New Zealand Application No. 729130 (tracked and clean), dated Nov. 24, 2017, (4 pages).
Extension of Time Granted and Notice of Opposition to Grant of Patent (Section 21) in corresponding New Zealand Patent Application No. 729130, Sep. 27, 2017 (3 pages).
First Office Action issued in related Japanese Application No. 2015-246225 with English translation, dated Sep. 8, 2016, 10 pages.
Second Office Action (Notice of Reasons for Rejection) issued in related Japanese Application No. JP 2014-46007 dated Aug. 8, 2016, with English translation (14 pages).
Examination Report issued in related European Application No. 14 198 923.6-1651 dated Feb. 10, 2016, 4 pages.
510(k) Premarket Notification—Invacare Twilight; http://www.accessdata.fda.gov/scripts/cdrh/cfdocs/cfPMN/pmn.cfm?ID=K022642, Mar. 16, 2017, 3 pages.
510(k) Summary—Invacare Corporation's Model Twilight Nasal Mask, K022642, Feb. 11, 2003, 5 pages.
User Manual for Invacare Twilight—Nasal Mask and Headgear—Model No. ISP2000 Large, 2003, 12 pages.
Decision of Rejection issued in related Japanese Application No. 2016-240978 dated Jun. 4, 2018, with English translation, 7 pages.
Examination Report issued in related European Application No. 12 190 819.8, dated Oct. 2, 2018, (4 pages).
Second Office Action issued in related Japanese Application No. 2016-240978, dated Nov. 5, 2018, with English translation (3 pages).
First Examination Report issued in related New Zealand Application No. 747187, dated Nov. 15, 2018, (2 pages).

* cited by examiner

HEADGEAR ASSEMBLY FOR A RESPIRATORY MASK ASSEMBLY

CROSS-REFERENCE TO PRIORITY APPLICATIONS

This is a continuation of U.S. application Ser. No. 13/865,496, filed Apr. 18, 2013, now U.S. Pat. No. 9,168,349, which is a continuation of U.S. application Ser. No. 13/200,947, filed Oct. 5, 2011, now U.S. Pat. No. 8,443,805, which is a continuation of U.S. application Ser. No. 12/285,445, filed Oct. 6, 2008, now U.S. Pat. No. 8,042,543, which is a continuation of U.S. application Ser. No. 10/655,602, filed Sep. 5, 2003, now U.S. Pat. No. 7,509,958, which claims priority to U.S. Provisional Application Ser. No. 60/424,694 filed Nov. 8, 2002, each of which is incorporated herein by reference in its entirety.

FIELD OF THE INVENTION

The present invention relates to a headgear assembly for use in holding a respiratory mask assembly in position on a patient's face, the mask assembly being used for treatment, e.g., of Sleep Disordered Breathing (SDB) with Non-invasive Positive Pressure Ventilation (NPPV).

BACKGROUND OF THE INVENTION

Respiratory mask assemblies such as the Mirage® nasal mask assembly manufactured by RedMed Ltd. and used for treatment of SDB such as Obstructive Sleep Apnea (OSA) are typically held in position on a patient's head by a headgear assembly. A headgear assembly typically includes a pair of side portions and a rear portion. The side portions are adapted to engage with the patient's mask and the rear portion is adapted to engage the back of the patient's head.

Headgear assemblies are structured to position and stabilize a patient interface, such as a nasal mask, on a patient's face so that a good seal can be maintained. In addition, the headgear assembly should be comfortable so that a patient can wear the mask assembly at night while they sleep. Many prior art headgear assemblies are uncomfortable to wear for long periods. It is desirable that one form of headgear assembly is suitable for a broad range of patients in order to reduce inventory, and ultimately reduce costs.

Completely rigid headgear assemblies are known, but they typically suffer from being uncomfortable to wear for long periods. In addition, because of their rigidity, they typically do not fit a broad range of patients, being suitable only for a subset.

For reasons of costs, it is desirable to be able to cut headgear assemblies from a flat piece of fabric or composite, yet in use the headgear assembly should conform to a complex three-dimensional shape. Hence a problem to overcome is to have a design of headgear assembly which can be easily manufactured by cutting or stamping, and yet in use be able to fit a wide range of head shapes and sizes.

Known forms of headgear assemblies include the Res-Cap™, ResCap™ II and MIRAGE® headgear, as shown in FIGS. 11-16. These headgear assemblies are constructed from fabric or composite layers of fabric and neoprene. Because of the soft flexible nature of the straps in the headgear assembly, there is the possibility of some movement of the headgear assembly on the patient's head, particularly during the course of a night's sleep. Hence, while the headgear assembly may be initially correctly positioned on a patient's head, they may subsequently move to an incorrect position.

A form of connector to enable the headgear assembly to engage with the patient's mask is taught in U.S. Pat. No. 6,374,826 (Gunaratnam et al.), the contents of which are hereby incorporated by reference.

U.S. Pat. No. 6,422,238 (Lithgow) shows a form of headgear assembly including a quick-release mechanism. The contents of the Lithgow patent are hereby incorporated by reference. The headgear assembly taught by Lithgow includes an upper and lower strap in each side portion extending between the patient's face and the rear of the patient's head. The upper straps lie above the ears on the patient's head. The lower straps lie below the ears on the patient's head.

A problem which can occur with prior art mask assemblies, such as the mask assemblies shown in FIGS. 11-16 and taught by Gunaratnam and Lithgow, is that the lower straps of the mask assemblies can ride up the patient's head while in use and cause chafing and irritation of the lower portion of the patient's ears.

SUMMARY OF THE INVENTION

One aspect of the present invention is directed towards a mask assembly having a headgear assembly that offers more comfort to the patient yet does not sacrifice functionality.

Another aspect of the present invention provides a respiratory mask assembly for delivering breathable gas to a patient. The respiratory mask assembly according to one embodiment includes a frame and a headgear assembly removably attachable to the frame. The headgear assembly includes a pair of side portions and a rear portion that interconnects the pair of side portions. The pair of side portions includes at least one strap. The rear portion has at least one strap constructed of at least two layers of material. One of the layers of material has a more rigid construction than the other of the layers of material to resist compression of the at least one strap of the rear portion in a first direction and thereby resist movement of the at least one strap of the pair of side straps in the first direction.

Another aspect of the invention is to provide a means for maintaining flexible headgear straps of a mask assembly in correct relative position on a patient's head in use.

Another aspect of the invention is to provide a comfortable headgear assembly for a mask assembly which fits a wide range of head shapes and sizes.

Another aspect of the invention is to provide a comfortable headgear assembly of a mask assembly which fits a wide range of patients and can be cut from a flat piece of fabric.

Other aspects, features and advantages of this invention will become apparent from the following detailed description when taken in conjunction with the accompanying drawings, which are part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
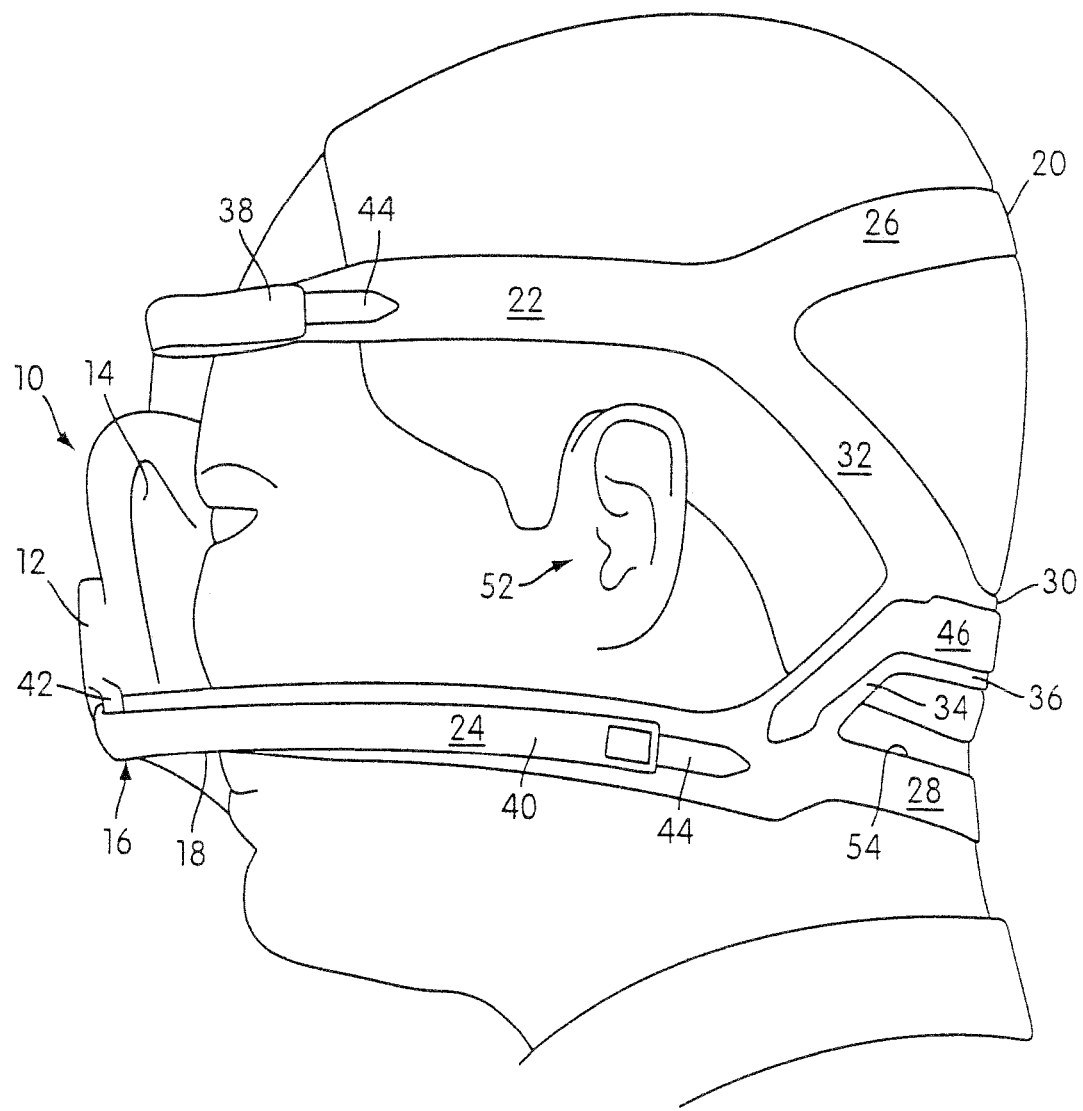
FIG. 1 is a side view illustrating a mask assembly having a headgear assembly constructed in accordance with an embodiment of the invention mounted on a patient's head.

FIG. 1 shows a respiratory mask assembly 10 that includes a frame 12 and a cushion 14 that may be permanently or removably connected to the frame 12. A headgear assembly 16 is removably attached to the frame 12 and is structured to maintain the frame 12 and cushion 14 in a desired adjusted position on a patient's face. In the illustrated embodiment, the mask assembly 10 is a nasal mask structured to deliver breathable gas to a patient's nose. However, the mask assembly 10 may be a nasal and mouth mask or the mask assembly 10 may be a full-face mask.

As shown in FIGS. 1-4, the headgear assembly 16 includes two side portions 18 with a rear portion 20 connecting the side portions 18. Each side portion 18 comprises an upper side strap 22 and a lower side strap 24. The rear portion 20, which interconnects the two side portions 18, includes a curved upper strap 26, a lower strap 28, and an intermediate strap arrangement 30 therebetween. The intermediate strap arrangement 30 is generally H-shaped and has a pair of upper straps 32, a pair of lower straps 34, and a cross-bar strap 36. The upper straps 32 are angled with respect to the curved upper strap 26 and the lower straps 34 are angled with respect to the lower strap 28. However, the straps of the headgear assembly 16 may have any suitable configuration to maintain the frame 12 and cushion 14 in a desired adjusted position on a patient's face. For example, the upper strap 26 may not be curved with respect to the upper straps 22 and the intermediate strap arrangement 30 may have any suitable shape, i.e., not H-shaped.

Figure 4:
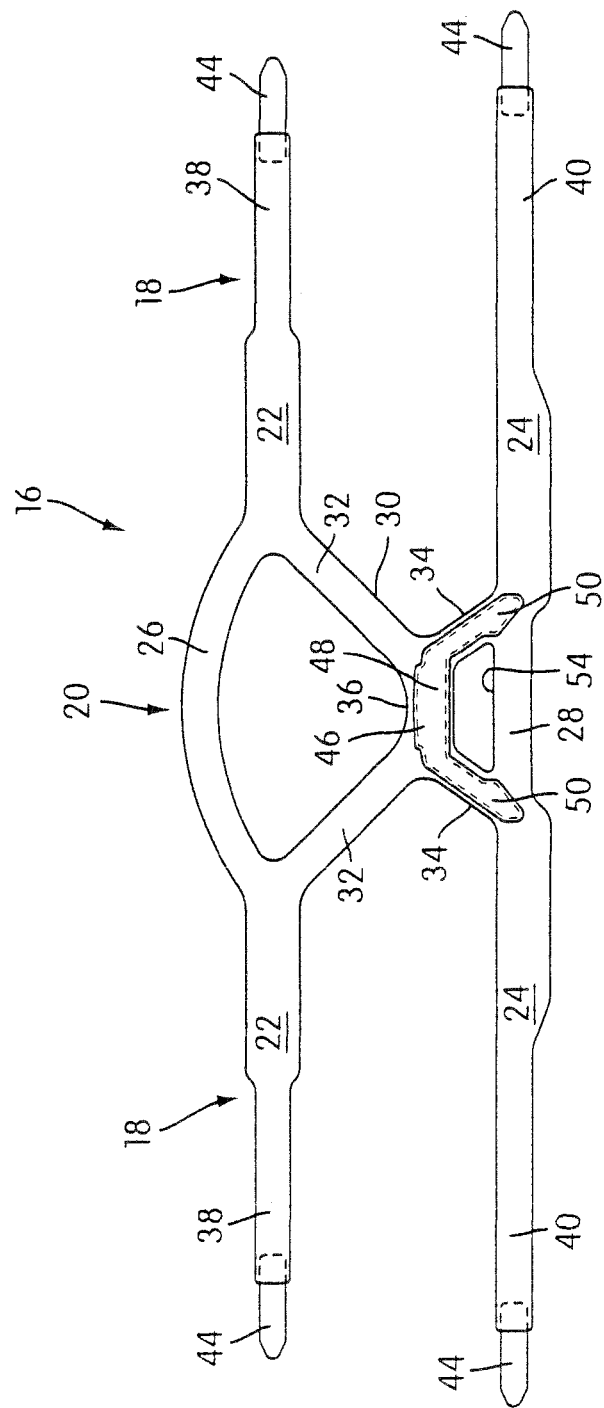
FIG. 4 is a top view illustrating the headgear assembly of FIG. 1 laid flat.

Each upper side strap 22 is removably connected to an upper portion of the frame 12 and each lower side strap 24 is removably connected to a lower portion of the frame 12. As shown in FIG. 4, the end portion 38, 40 of each upper and lower strap 22, 24, respectively, has a reduced width that enables each upper and lower strap 22, 24 to be wrapped around a respective clip structure 42 (see FIG. 1) provided on the frame 12. Fastening of the upper and lower straps 22, 24 to the frame 12 may be assisted by use of a hook and loop material, such as VELCRO®. As shown in FIG. 4, the free end of each upper and lower strap 22, 24 includes a strip of hook material 44 attached thereto by stitching, for example. The upper and lower straps 22, 24 are constructed of a loop material that engages the strip of hook material 44 when the upper and lower straps 22, 24 are connected to the frame 12.

However, the upper and lower straps 22, 24 may be connected to the frame 12 in any other suitable manner. For example, the upper and lower straps 22, 24 may include locking clips attached thereto that are adapted to interlockingly engage with the frame 12. Alternatively, the upper and lower straps 22, 24 may be magnetically coupled with the frame 12 so as to interconnect the frame 12 and headgear assembly 16. Further, the frame 12 may include a forehead support movably mounted to an upper portion thereof. In such an arrangement, the upper straps 22 may be removably connected to clip structures provided on the forehead support.

Figure 7:
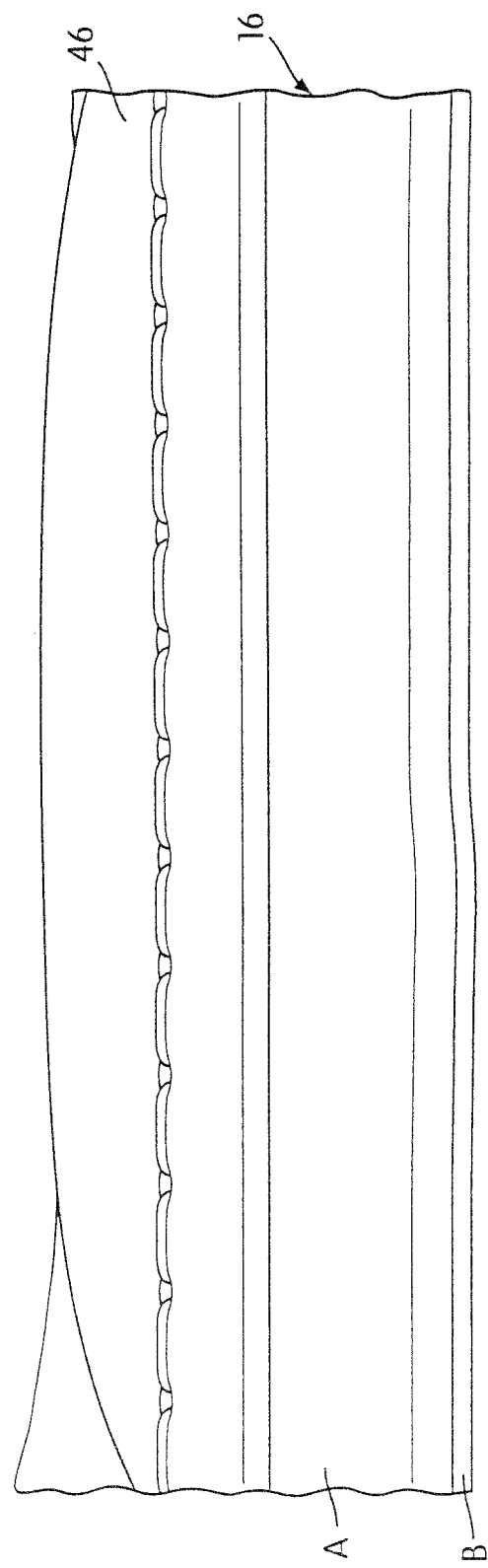
FIG. 7 is an enlarged photographic side view illustrating an embodiment of a stiffener of the headgear assembly of FIG. 1.

The straps of the headgear assembly 16 are constructed from a soft, flexible composite material such as Breathe-O-Prene™ manufactured by Accumed Technologies, Inc. As shown in FIG. 7, the straps include two layers of material A, B with one of the layers A having a loop material to facilitate the connection with the strip of hook material 44 provided on the free ends the upper and lower straps 22, 24. However, the straps may be constructed from any other suitable soft, flexible material.

In the illustrated embodiment, a stiffener 46 is attached to the rear portion 20 of the headgear assembly 16. As shown in FIGS. 2 and 4-6, the stiffener 46 has a general C-shape including a body 48 and a pair of arm members 50. The stiffener 46 is attached to the H-shaped intermediate strap arrangement 30 such that the body 48 of the stiffener 46 extends along the cross-bar strap 36 and the arm members 50 of the stiffener 46 extend along respective lower straps 34. The body 48 has a width that is greater than a width of the arm members 50. Further, the free ends of the arm members 50 have a greater width than the remaining portion of the arm members 50. However, the stiffener 46 may have any suitable structure and width dimensions. The stiffener 46 is constructed from a semi-rigid skin-compatible material such as thermoplastics, e.g., nylon or polyester or a thermoplastic elastomer, e.g. santoprene. The stiffener 46 has a thickness in the range of 0.8 mm to 1.5 mm, preferably 1 mm.

Figure 5:
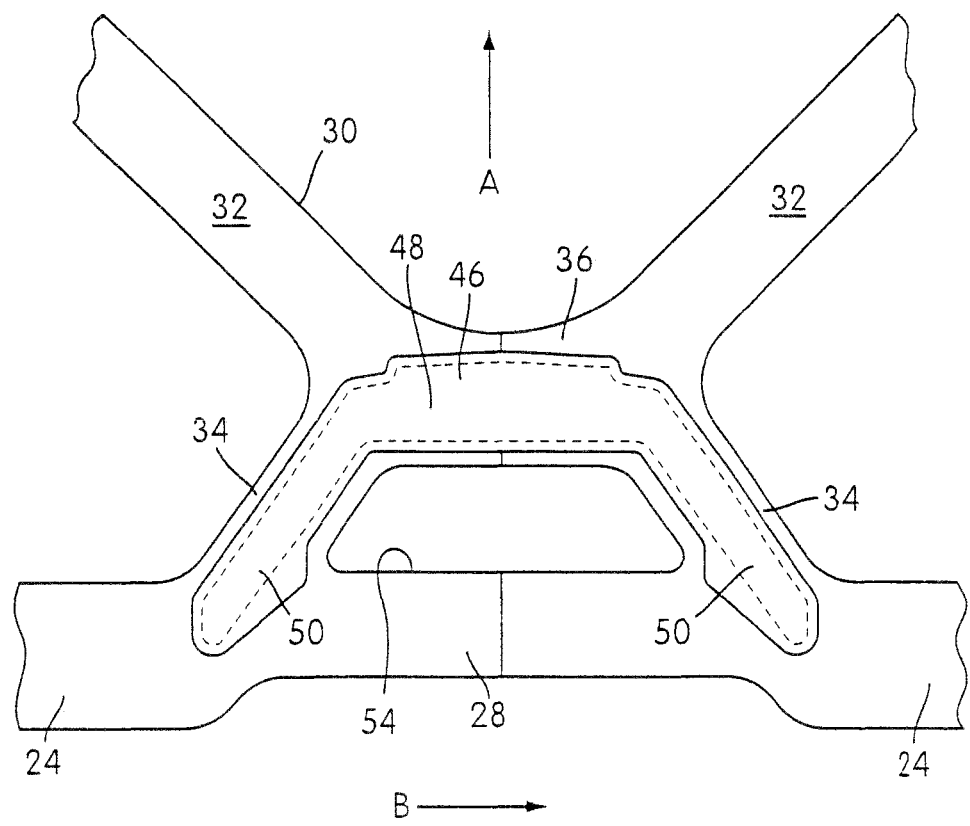
FIG. 5 is an enlarged top view illustrating an embodiment of a stiffener of the headgear assembly of FIG. 1.
Figure 6:
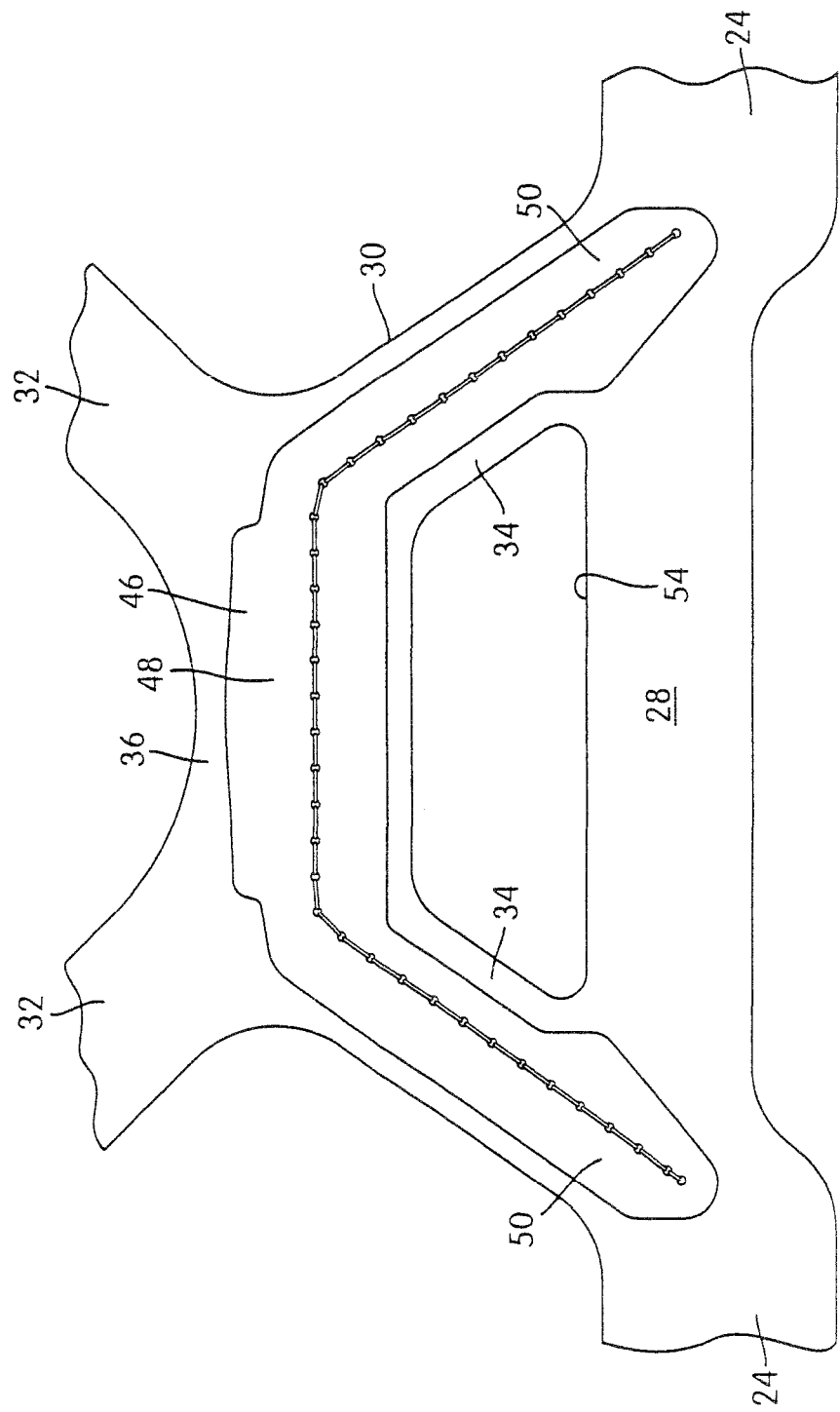
FIG. 6 is an enlarged photographic top view illustrating an embodiment of a stiffener of the headgear assembly of FIG. 1.

The stiffener 46 is attached to the corresponding straps 34, 36 with adhesives, stitching, or other known attachment mechanisms or by semi-permanent means such as velcro, pocket sleeve, etc. As shown in FIG. 5, the stiffener 46 is secured to the straps 34, 36 by stitching around the periphery of the stiffener 46. As shown in FIG. 6, the stiffener 46 is secured to the straps by stitching an intermediate portion of the stiffener 46. FIG. 7 is an enlarged view that illustrates the stiffener 46 secured to the straps by stitching. The stitch line is in the range of 2-3 mm, preferably 2.5 mm, from the edge of the stiffener 46.

The stiffener 46 is narrower than the straps 34, 36 so that when the stiffener 46 is attached to the straps 34, 36, the softer material of the straps 34, 36 extends beyond the more rigid material of the stiffener 46, thereby preventing or at least reducing the opportunity for contact between the patient and the more rigid material of the stiffener 46 that could cause irritation or discomfort.

The stiffener 46 adds to the rigidity of the headgear assembly 16 in certain planes and directions, which assists in stabilizing the mask assembly 10 on the head of the patient during use. In other planes and directions, the headgear assembly 16 has a different rigidity.

Figure 2:
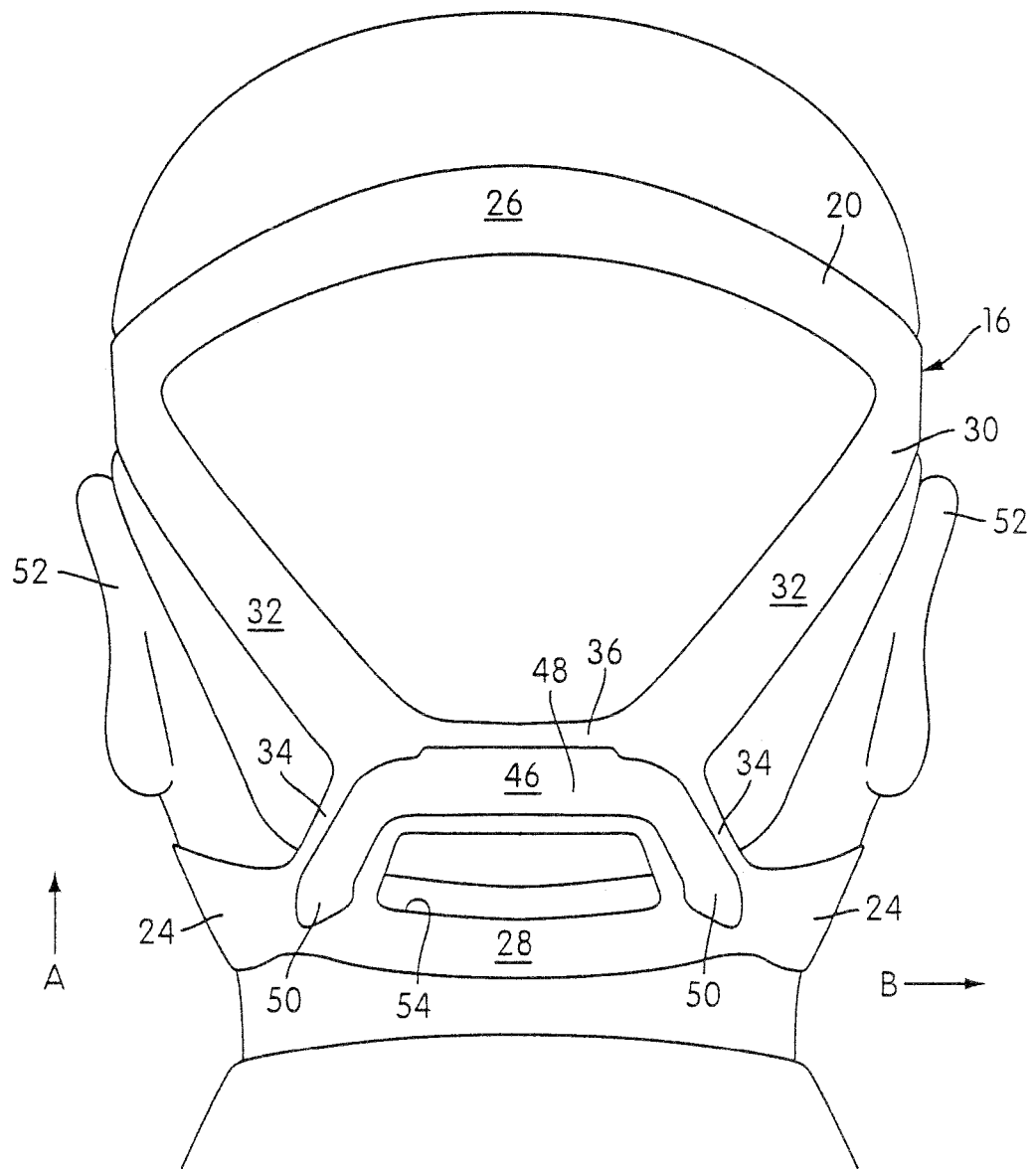
FIG. 2 is a rear view illustrating the headgear assembly of FIG. 1 mounted on a patient's head.
Figure 3:
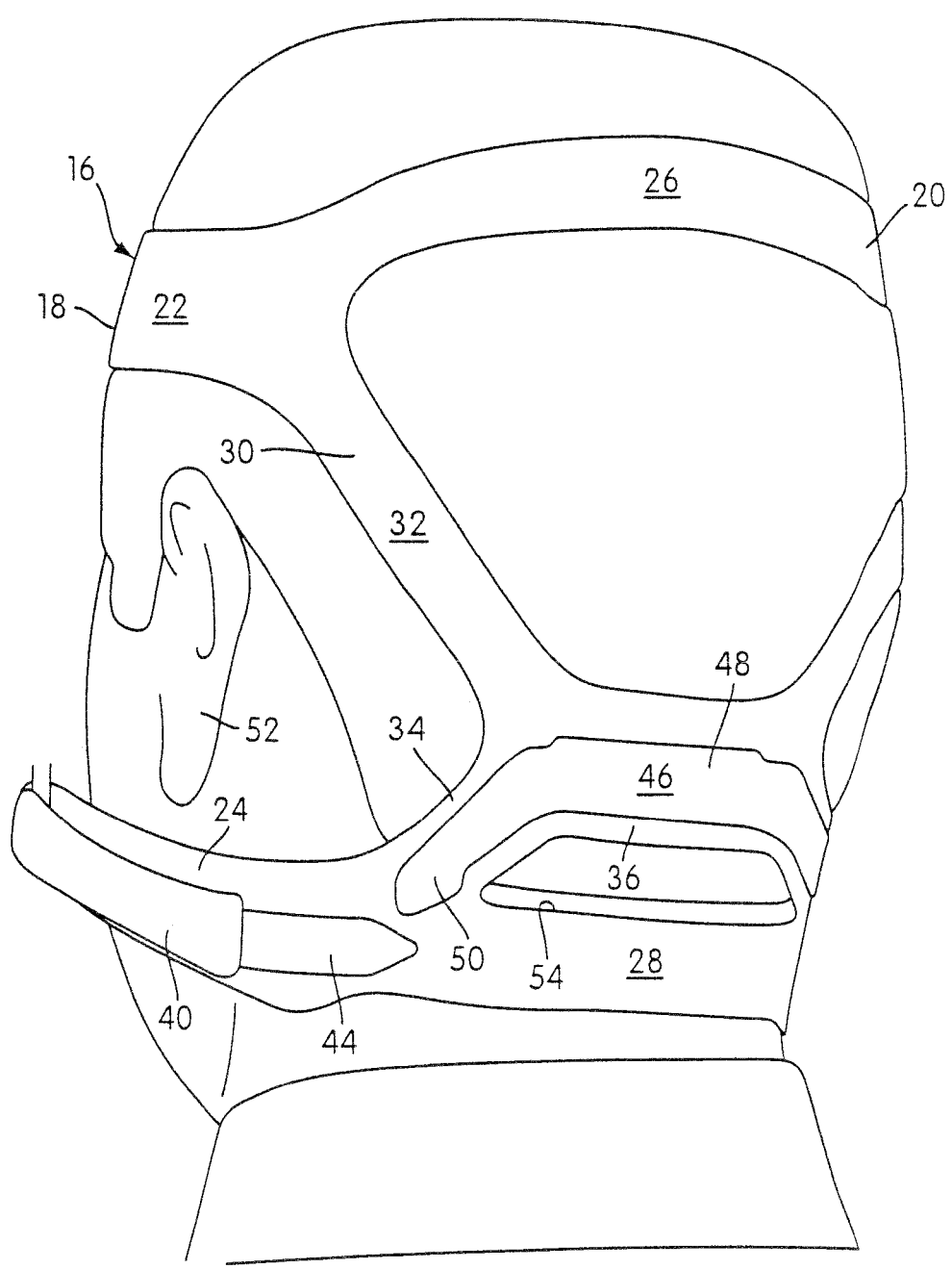
FIG. 3 is a rear perspective view illustrating the headgear assembly of FIG. 1 mounted on a patient's head.

For example, the stiffener 46 reduces the flexibility of the straps 34, 36 at the back of the patient's head along the direction of arrow A or in a reverse direction of arrow A, as shown in FIG. 2. The presence of the stiffener 46 stops compression of the straps 34, 36 along the reverse direction of arrow A. In this way, the straps 34, 36 and stiffener 46 should be able to resist the riding up of the lower straps 24 towards the patient's ears 52. In general, the straps 34, 36 and stiffener 46 should be able maintain their positions with respect to the head of the patient when the straps 34, 36 and stiffener 46 are connected to the frame 12. Thus, the likelihood that the lower straps 24 will ride up into the lower portion of the ears 52 of the patient is reduced.

Further, the headgear assembly 16 is shaped to avoid interference with the patient's ears 52. In particular, the upper side strap 22 is connected to the frame 12 above the patient's eyes and patient's ears 52. The lower side strap 24 is connected to the frame 12 and extends below the patient's ear 52. The upper straps 32 and lower straps 34 interconnect the upper and lower straps 22, 24 and are angled sufficiently away from the patient's ears 52. Also, the upper and lower straps 32, 34 are of sufficient length to space the upper and lower straps 22, 24 from the patient's ears 52. Due to the added rigidity provided by the stiffener 46, all the straps of the headgear assembly 16 are better able to maintain a predetermined shape. The thickness of the stiffener 46 may vary across its profile to modify flexibility characteristics, for example, thicker regions may be stiffer.

On the other hand, a certain degree of flexibility of the headgear assembly 16 is provided such that variations in patient physiology can be accommodated to a certain degree. For example, the lower strap 28 has relatively more flexibility along arrow direction B or its reverse direction than straps 34, 36 with the stiffener 46 attached.

The H-shaped intermediate strap arrangement 30 of the headgear assembly 16 also helps maintain the headgear assembly 16 in a desired adjusted position on the patient. As shown in FIG. 1, the curved upper strap 26 extends across a rear upper portion of the patient's head and the lower strap 28 and cross-bar strap 36 extend across a rear lower portion of the patient's neck and head, respectively. More specifically, the curved upper strap 26 is structured to engage a posterior portion of the parietal bone of the patient's head in order to prevent downward movement of the headgear assembly 16 opposite the direction of arrow A in FIG. 2. The cross-bar strap 36 is structured to engage a lower portion of the occipital bone of the patient's head and the lower strap 28 is structured to engage a rear upper portion of the patient's neck. As a result, the cross-bar strap 36 and the lower strap 28 prevent upward movement of the headgear assembly 16 in the direction of arrow A in FIG. 2. Moreover, the stiffener 46 is structured to resist the riding up of the lower straps 34 and hence the lower straps 24 towards the patient's ears 52. However, the intermediate strap arrangement 30 may have any suitable configuration to maintain the frame 12 and cushion 14 in a desired adjusted position on a patient's face.

Further, the straps 28, 34, and 36 form an opening 54 therebetween that can accommodate any skin folds of a patient which may extend through the opening 54. Specifically, movement of the patient's head can create a fold of skin adjacent the patient's neck. The straps 28, 34, and 36 are structured and positioned on the patient's head such that any skin folds will extend through the opening 54 and not adversely affect the positioning of the headgear assembly 16 on the patient's head. The opening 54 formed between the straps 28, 34, and 36 may have any suitable shape, i.e., trapezoidal or non-trapezoidal shape. The reduced width of strap 28 allows it to stretch over the fatter lower neck, that is, there is a different stretch between strap 36 and strap 28.

Figure 8:
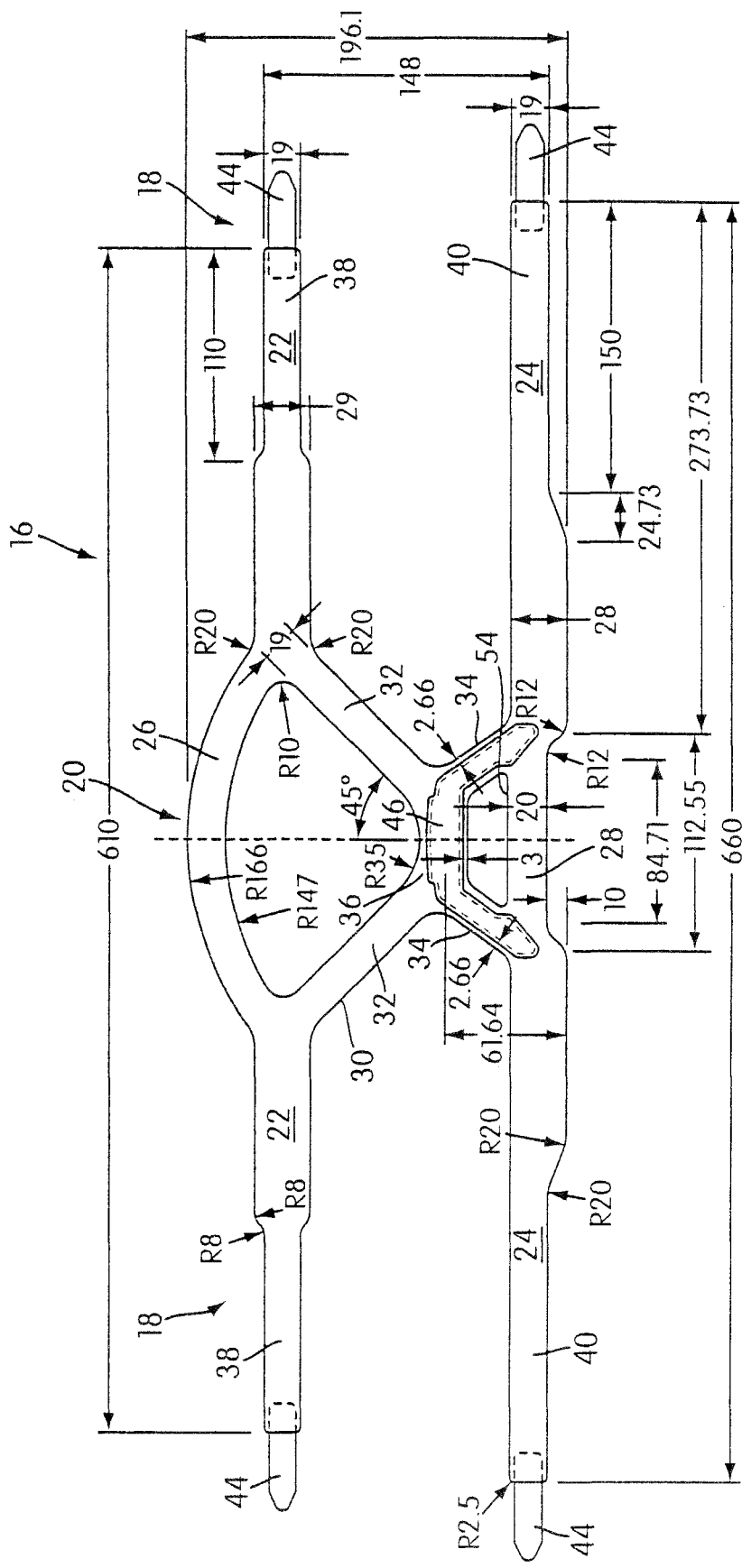
FIG. 8 is a top view illustrating the headgear assembly of FIG. 1 laid flat and showing typical dimensions of an embodiment (R-radius)

FIG. 8 illustrates dimensions of an embodiment of the headgear assembly 16. For example, the overall length of the headgear assembly 16 is in the range of 640-680 mm, preferably 660 mm and the overall height of the headgear assembly 16 is in the range of 175-215 mm, preferably 196.1 mm. The upper straps 32 are angled in the range of 40-50°, preferably 45°, with respect to the upper straps 22 and have a width in the range of 16-22 mm, preferably 19 mm. The curved upper strap 26 has a radius of curvature in the range of 145-170 mm, preferably 166 mm. Further, the lower strap 28 has a width in the range of 17-23 mm, preferably 20 mm, and the end portions 38, 40 of the upper and lower straps 22, 24 have a width in the range of 16-23 mm, preferably 19 mm. In an embodiment of the headgear assembly 16, the dimensions illustrated in FIG. 8 vary ±10%.

Figure 9:
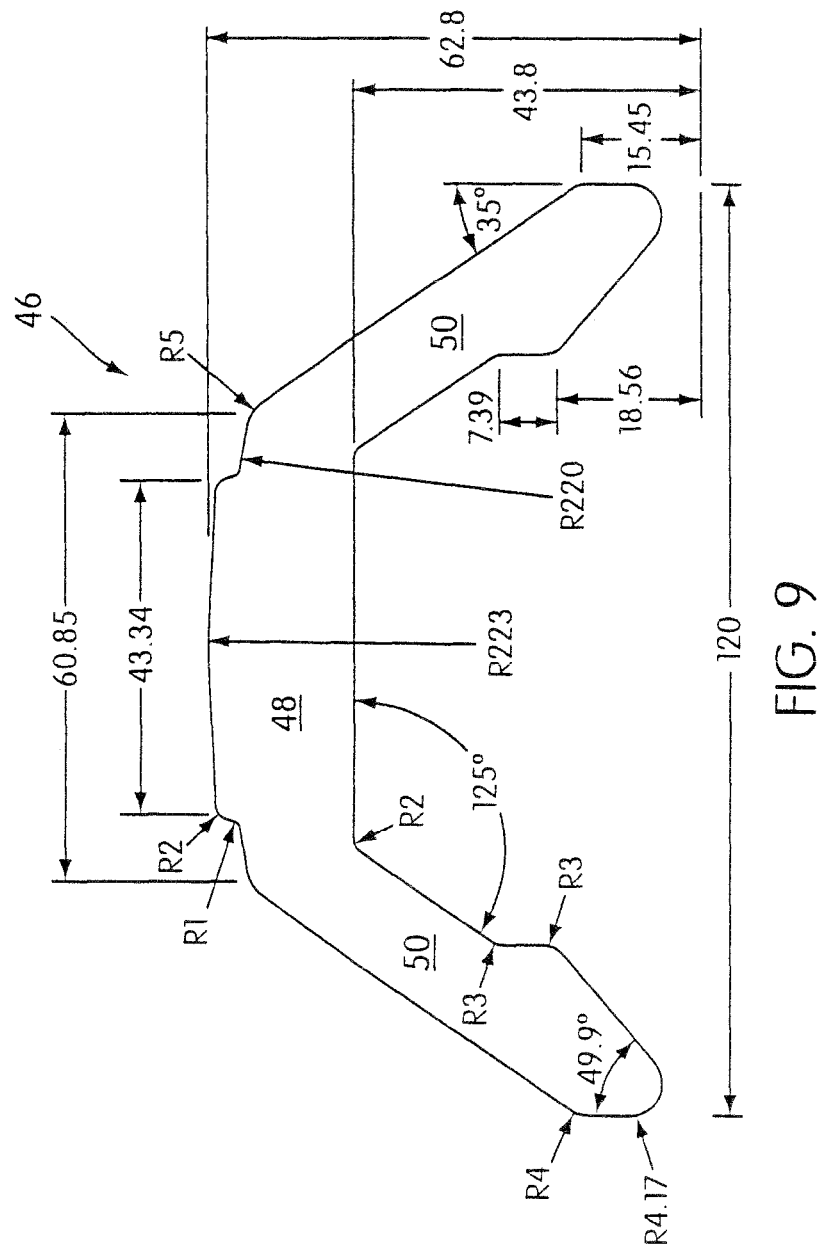
FIG. 9 is a top view illustrating an embodiment of a stiffener of the headgear assembly of FIG. 1 and showing typical dimensions of an embodiment (R-radius)

FIG. 9 illustrates dimensions of an embodiment of the stiffener 46. For example, the overall length of the stiffener 46 is in the range of 100-140 mm, preferably 120 mm and the overall height of the stiffener 46 is in the range of 40-80 mm, preferably 62.8 mm. The arm members 50 are angled in the range of 110-140°, preferably 125°, with respect to the body 48. In an embodiment of the stiffener 46, the dimensions illustrated in FIG. 9 vary ±10%.

Figure 10:
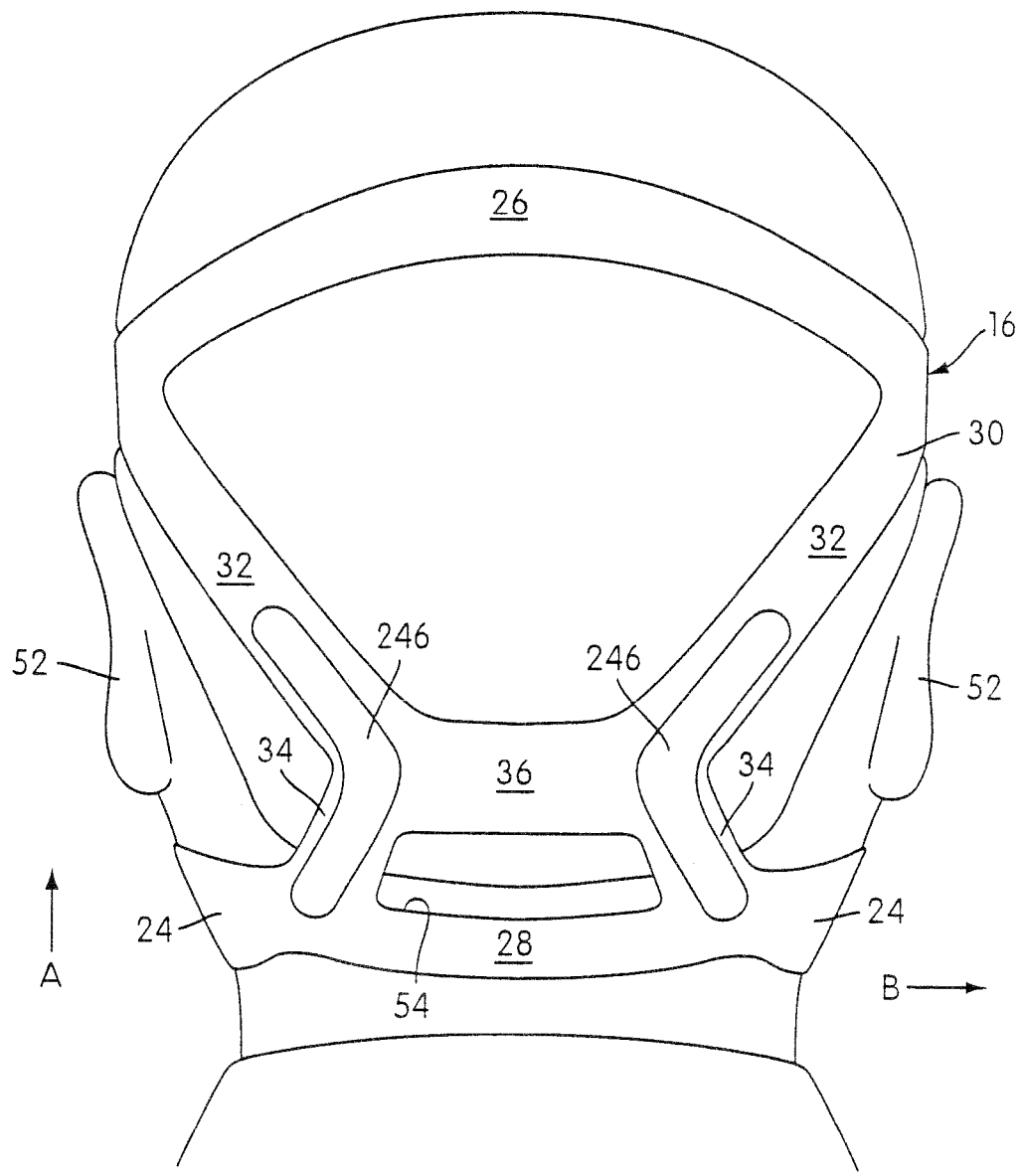
FIG. 10 is a rear view illustrating a headgear assembly constructed in accordance with another embodiment of the invention mounted on a patient's head.
Figure 11:
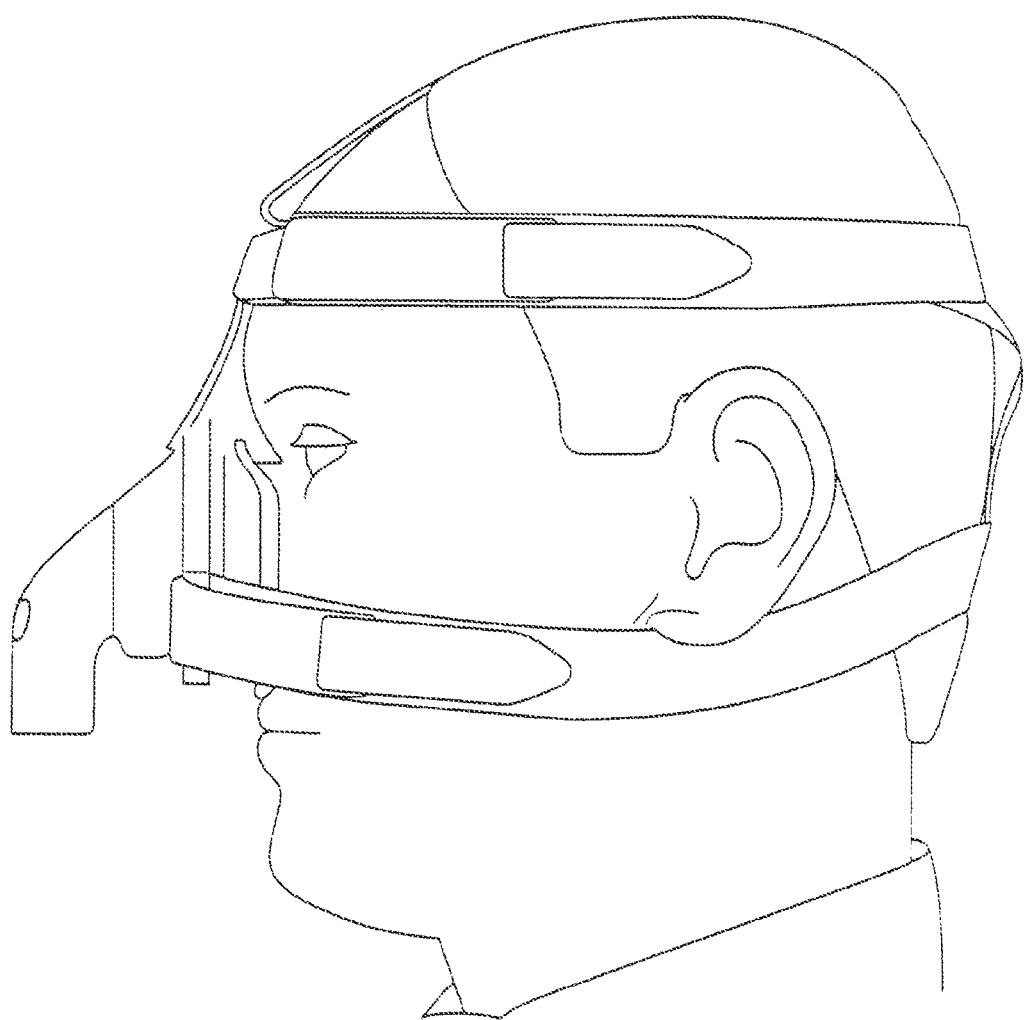
FIG. 11 is a side view of a prior art ResCap™ headgear assembly.
Figure 12:
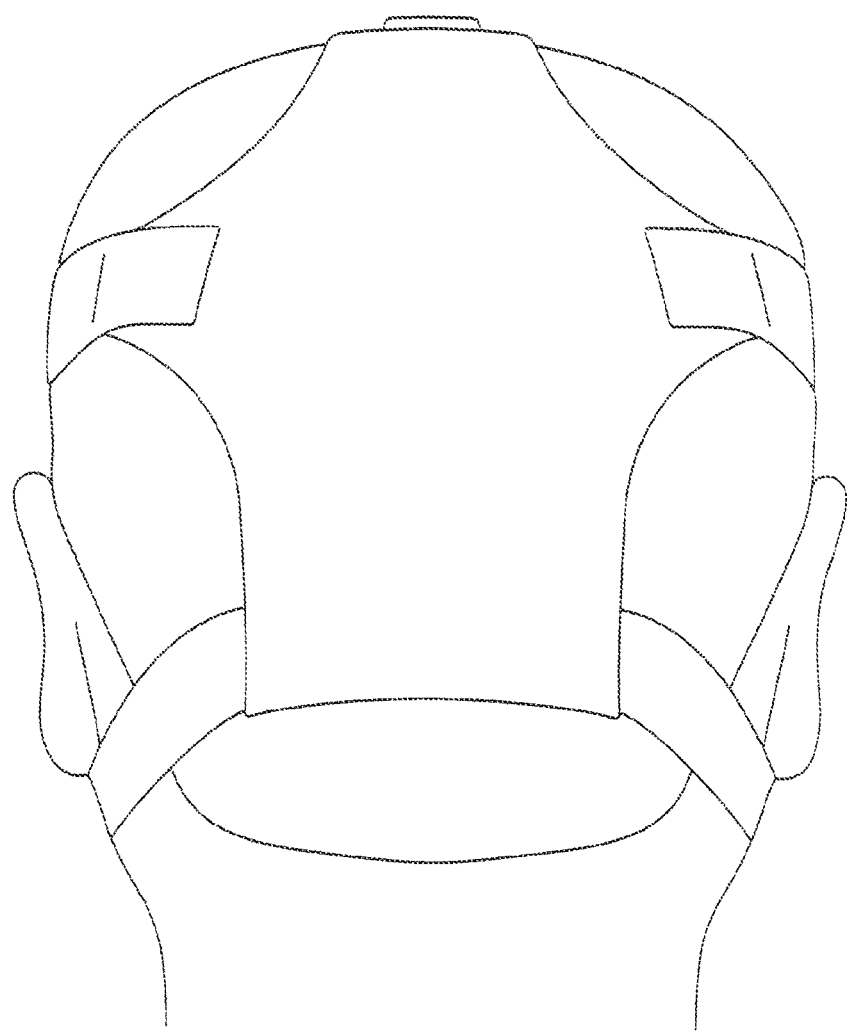
FIG. 12 is a rear view of a prior art ResCap™ headgear assembly.
Figure 13:
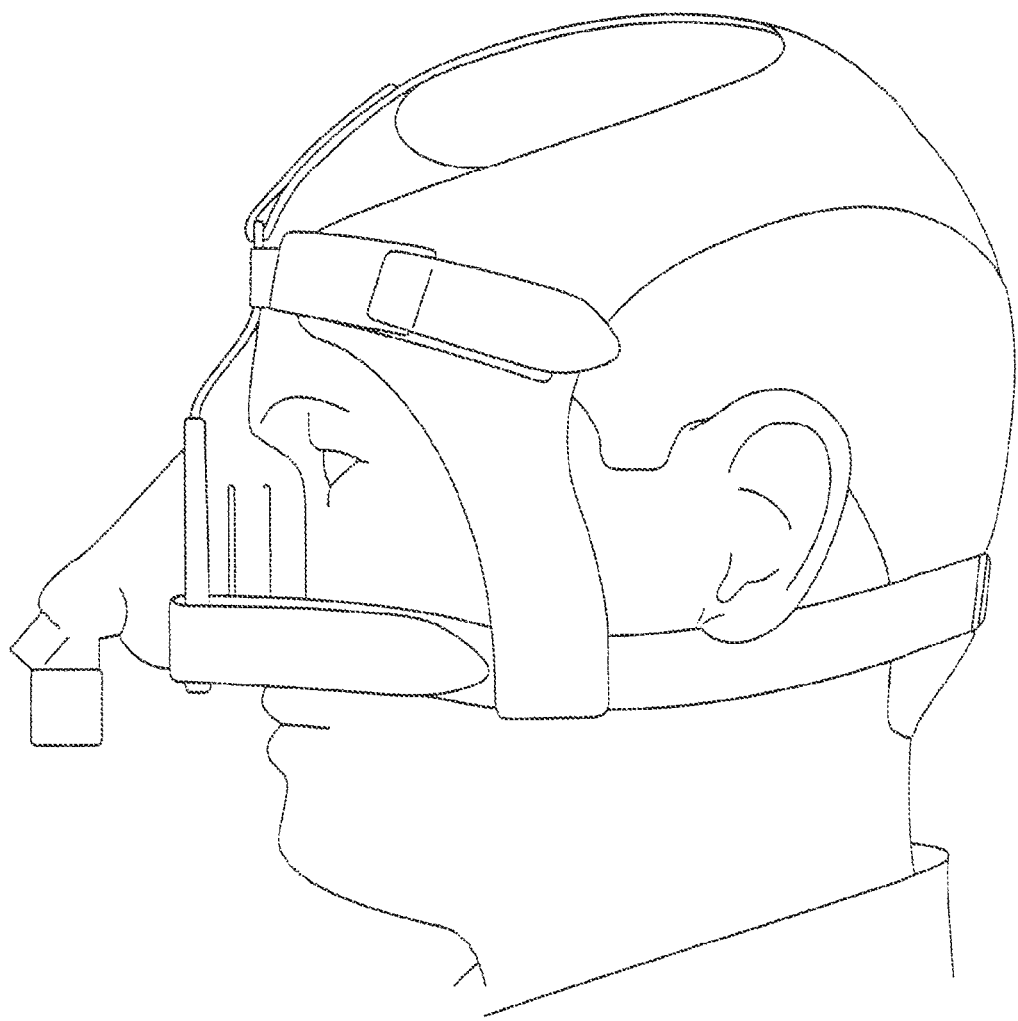
FIG. 13 is a side view of a prior art ResCap™ II headgear assembly.
Figure 14:
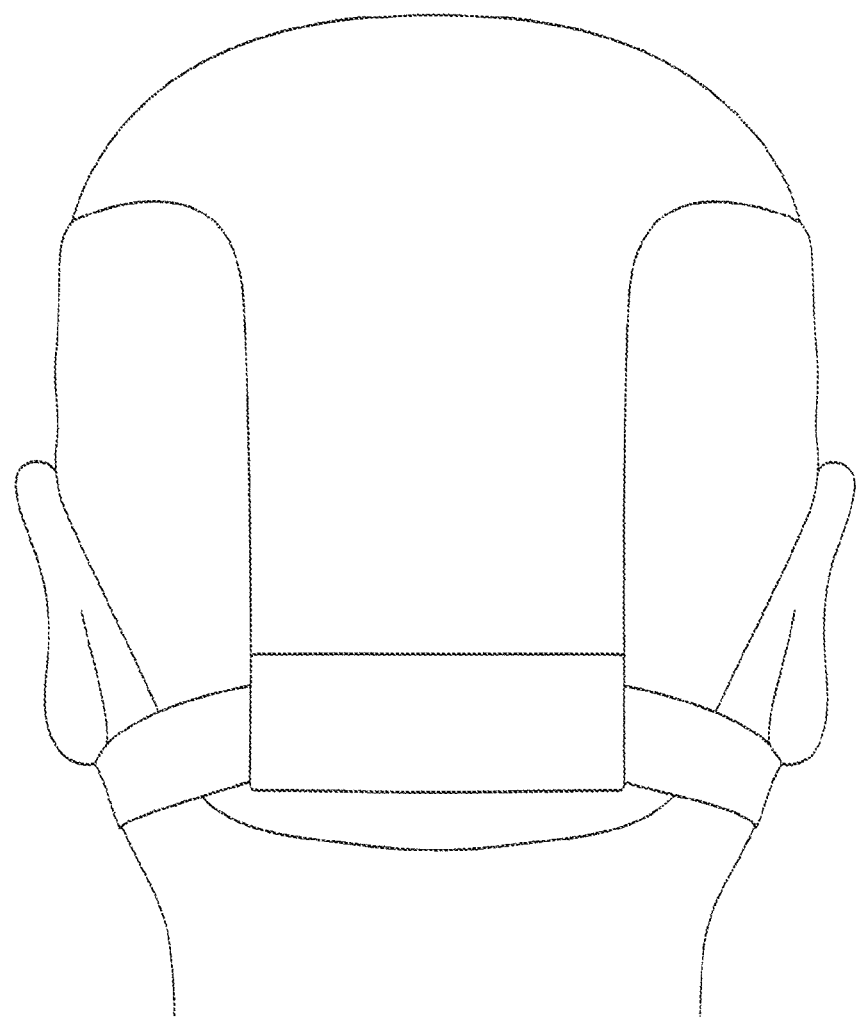
FIG. 14 is a rear view of a prior art ResCap™ II headgear assembly.
Figure 15:
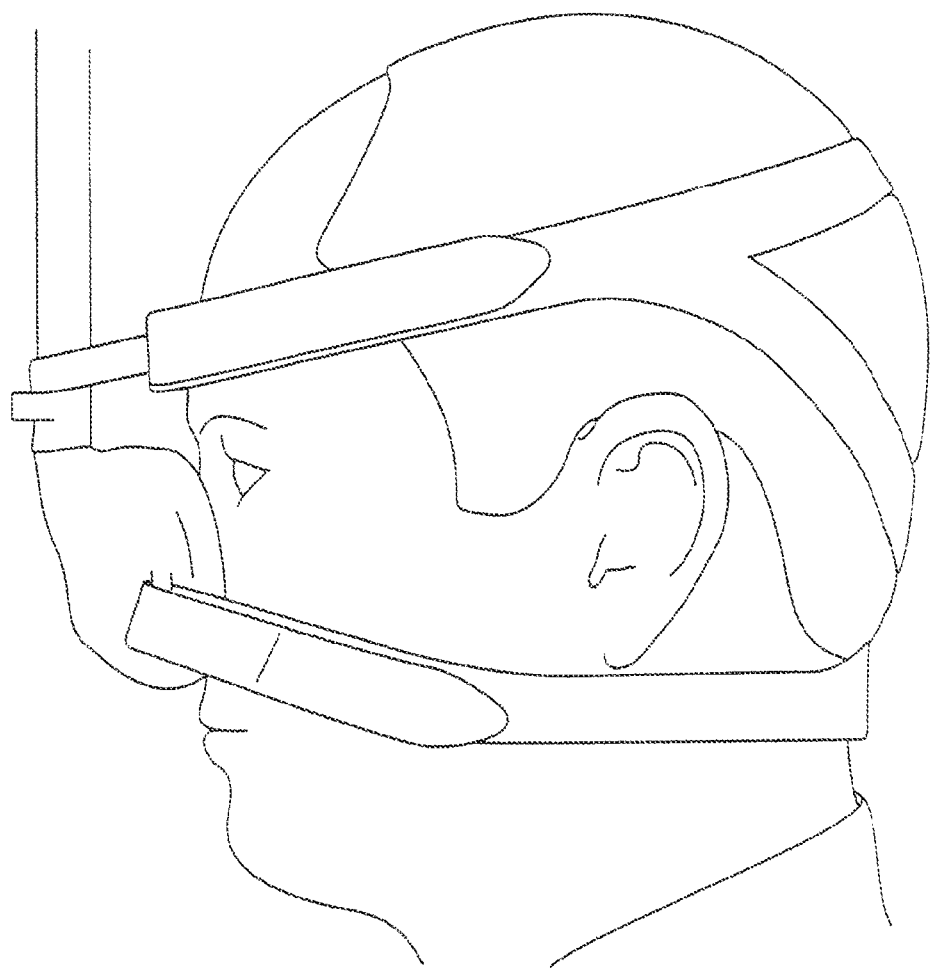
FIG. 15 is a side view of a prior art MIRAGE® headgear assembly.
Figure 16:
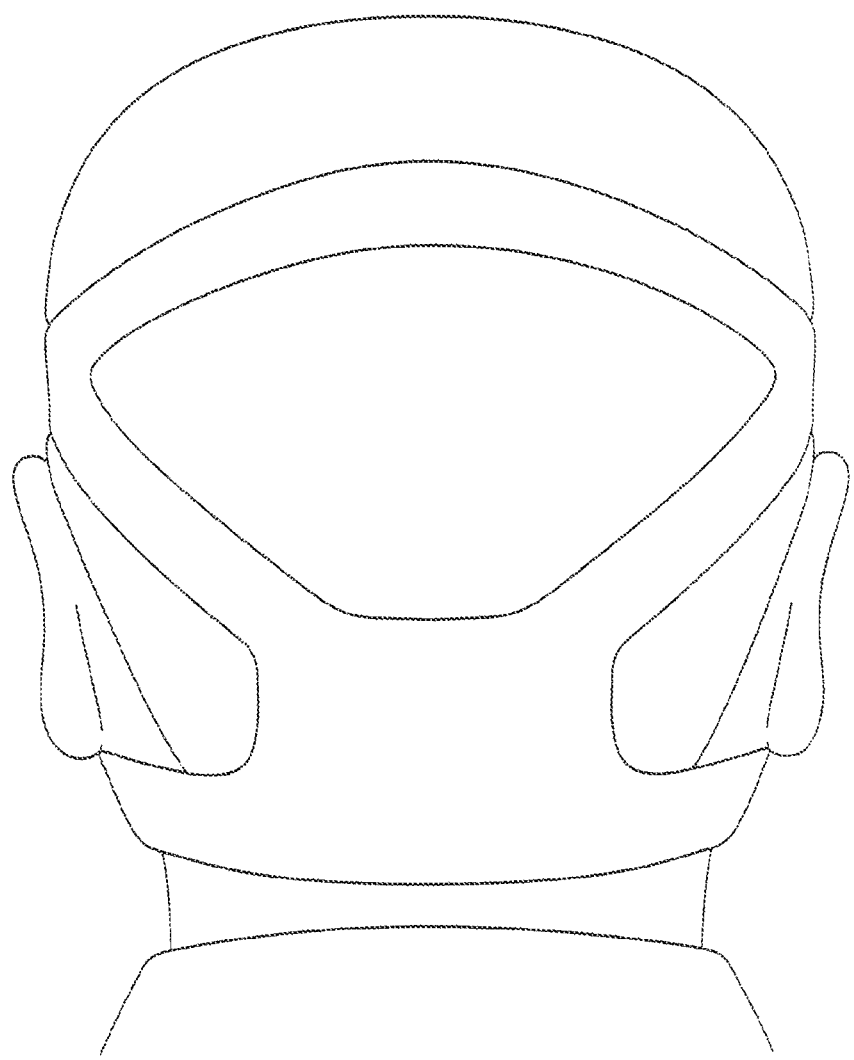
FIG. 16 is a rear view of a prior art MIRAGE® headgear assembly.

FIG. 10 illustrates another embodiment of the stiffener, indicated as 246. In this embodiment, the stiffener is in the form of a pair of arcuate-shaped stiffeners 246. Each stiffener 246 extends along the upper strap 32, across the cross-bar strap 36, and along the lower strap 34. Similar to the stiffener 46, the stiffeners 246 reduces the flexibility of the straps 32, 34, and 36 at the back of the patient's head along the direction of arrow A or in a reverse direction of arrow A, so as to resist the riding up of the lower straps 24 towards the patient's ears 52.

The straps of the headgear assembly 16 and the stiffener 46, 246 may be formed of a single material, so long as patient comfort and the appropriate rigidity/flexibility are maintained.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modification, alterations and substitutions within the spirit and scope of the detailed description.

What is claimed is:

1. A respiratory mask assembly configured to deliver breathable gas to a patient to treat sleep disordered breathing by providing non-invasive positive pressure ventilation to the patient during sleep, the respiratory mask assembly comprising:

a nasal mask comprising:

a mask frame having a forehead support; and a cushion removably connected to the mask frame, the cushion configured to seal against the patient's face to deliver breathable gas to the patient's nose during treatment; and a headgear assembly configured to stabilize and position the nasal mask to maintain the nasal mask in a desired adjusted position on the patient's face during treatment, the headgear assembly comprising:

a first upper side strap portion and a second upper side strap portion, each of the first upper side strap portion and the second upper side strap portion configured to extend across a corresponding lateral side of the patient's head and superior to the patient's corresponding ear and eye in use, and each of the first upper side strap portion and the second upper side strap portion having a free end;

a first lower side strap portion and a second lower side strap portion, each of the first lower side strap portion and the second lower side strap portion configured to extend across a corresponding lateral side of the patient's head from posterior to the patient's corresponding ear to anterior to the patient's corresponding ear and inferior to the patient's corresponding ear in use, and each of the first lower side strap portion and the second lower side strap portion having a free end;

an upper strap portion connecting the first upper side strap portion and the second upper side strap portion and configured to resist movement of the headgear assembly in an inferior direction on the patient's head in use;

a rear lower strap portion connecting the first lower side strap portion and the second lower side strap portion;

a rear cross-bar strap portion configured to be positioned inferior to the upper strap portion and superior to the rear lower strap portion in use;

a first upper intermediate strap portion and a second upper intermediate strap portion, each of the first upper intermediate strap portion and the second upper intermediate strap portion connecting a corresponding one of the first upper side strap portion and the second upper side strap portion to the rear cross-bar strap portion;

a first lower intermediate strap portion and a second lower intermediate strap portion, each of the first lower intermediate strap portion and the second lower intermediate strap portion connecting the rear cross-bar strap portion to the rear lower strap portion;

an upper opening defined between the upper strap portion and the rear cross-bar strap portion; and a rear lower opening defined between the rear lower strap portion and the rear cross-bar strap portion and configured to be positioned inferior to the upper opening in use, wherein the first upper intermediate strap portion and the second upper intermediate strap portion and the first lower intermediate strap portion and the second lower intermediate strap portion are oriented to avoid contact with the patient's ears in use, wherein each of the first upper side strap portion and the second upper side strap portion and each of the first lower side strap portion and the second lower side strap portion are constructed from a composite material, the composite material comprising a first layer of material configured to be positioned against the patient's head in use and a second layer of material further comprising a loop material, wherein a strip of hook material is attached to the composite material adjacent to the free end of each of the first upper side strap portion, the second upper side strap portion, the first lower side strap portion, and the second lower side strap portion, each strip of hook material and the loop material being configured to form a hook-and-loop connection, and wherein the upper opening and the rear lower opening are dimensioned such that the upper opening is configured to accommodate a larger portion of the patient's head in use than the rear lower opening.

2. The respiratory mask assembly according to claim 1, wherein one of the first layer of material and the second layer of material has a more rigid construction than the other of the first layer of material and the second layer of material to resist compression of the rear lower strap portion in a superior direction in use and thereby resist movement of the first lower side strap portion and the second lower side strap portion in the superior direction.

3. The respiratory mask assembly according to claim 1, wherein the upper opening is further defined by the first upper intermediate strap portion and the second upper intermediate strap portion, and the rear lower opening is further defined by the first lower intermediate strap portion and the second lower intermediate strap portion.

4. The respiratory mask assembly according to claim 1, wherein the rear cross-bar strap portion, the first lower intermediate strap portion, the second lower intermediate strap portion, the first upper intermediate strap portion, and the second upper intermediate strap portion are configured to engage the patient's head posterior the patient's ears in use.

5. The respiratory mask assembly according to claim 1, wherein the rear lower strap portion is configured to extend across a lower, rear portion of the patient's neck in use, and the rear cross-bar strap portion is configured to extend across a lower, rear portion of the patient's head in use.

6. The respiratory mask assembly according to claim 5, wherein the rear cross-bar strap portion is configured to engage a lower portion of the patient's occipital bone in use.

7. The respiratory mask assembly according to claim 5, wherein the rear cross-bar strap portion and the rear lower strap portion are configured to resist movement of the headgear assembly in a superior direction on the patient's head in use.

8. The respiratory mask assembly according to claim 1, wherein the upper strap portion is configured to extend across an upper portion of the patient's head in use.

9. The respiratory mask assembly according to claim 1, wherein the upper strap portion is configured to engage a portion of the patient's parietal bones in order to resist movement of the headgear assembly in the inferior direction on the patient's head in use.

10. The respiratory mask assembly according to claim 1, wherein the upper opening and the rear lower opening are configured to be oriented on the patient in use such that the upper opening and the rear lower opening are substantially bisected by the patient's median plane.

11. The respiratory mask assembly according to claim 1, wherein a lowermost edge of the rear lower strap portion is configured to be positioned superior to a lowermost edge of each of the first lower side strap portion and the second lower side strap portion on the patient's head in use.

12. The respiratory mask assembly according to claim 1,
wherein the upper opening is further defined by the first upper intermediate strap portion and the second upper intermediate strap portion, and the rear lower opening is further defined by the first lower intermediate strap portion and the second lower intermediate strap portion, wherein the rear cross-bar strap portion, the first lower intermediate strap portion, the second lower intermediate strap portion, the first upper intermediate strap portion, and the second upper intermediate strap portion are configured to engage the patient's head posterior to the patient's ears in use, wherein the upper strap portion is configured to extend across an upper portion of the patient's head in use, wherein the upper opening and the rear lower opening are configured to be oriented on the patient in use such that the upper opening and the rear lower opening are substantially bisected by the patient's median plane, wherein a lowermost edge of the rear lower strap portion is configured to be positioned superior to a lowermost edge of each of the first lower side strap portion and the second lower side strap portion on the patient's head in use, wherein the rear cross-bar strap portion is wider than the rear lower strap portion, and wherein the rear lower strap portion is configured to extend across a lower, rear portion of the patient's neck in use, and the rear cross-bar strap portion is configured to extend across a lower, rear portion of the patient's head in use.

13. The respiratory mask assembly according to claim 1, wherein the first upper side strap portion and the second upper side strap portion are configured to be attached to the forehead support and the first lower side strap portion and the second lower side strap portion are configured to be attached to the mask frame.

14. The respiratory mask assembly according to claim 13, further comprising a clip structure configured to attach each of the first lower side strap portion and the second lower side strap portion to the mask frame, wherein each of the first lower side strap portion and the second lower side strap portion is configured to be wrapped around a corresponding clip structure.

15. The respiratory mask assembly according to claim 13, wherein each of the first upper side strap portion and the second upper side strap portion is configured to be attached to the forehead support superior to the patient's corresponding eye and ear in use, and each of the first lower side strap portion and the second lower side strap portion is configured to be attached to the mask frame inferior to the patient's corresponding eye and ear in use.

16. The respiratory mask assembly according to claim 1, wherein the rear cross-bar strap portion is wider than the rear lower strap portion.

17. A respiratory mask assembly configured to deliver breathable gas to a patient to treat sleep disordered breathing by providing non-invasive positive pressure ventilation to the patient during sleep, the respiratory mask assembly comprising:
a nasal mask comprising:
a mask frame having a forehead support; and
a cushion removably connected to the mask frame, the cushion configured to seal against the patient's face to deliver breathable gas to the patient's nose during treatment; and a headgear assembly configured to stabilize and position the nasal mask to maintain the nasal mask in a desired adjusted position on the patient's face during treatment, the headgear assembly comprising:
a first side portion and a second side portion, each of the first side portion and the second side portion including an upper side strap portion configured to extend above the patient's corresponding ear and eye in use and a lower side strap portion configured to extend below the patient's corresponding ear in use;
an upper strap portion;
a rear lower strap portion; and
an intermediate rear strap arrangement between the upper strap portion and the rear lower strap portion, wherein the intermediate rear strap arrangement comprises a first upper intermediate strap portion, a second upper intermediate strap portion, a first lower intermediate strap portion, a second lower intermediate strap portion, and a cross-bar strap portion, wherein the first upper intermediate strap portion, the second upper intermediate strap portion, the first lower intermediate strap portion, and the second lower intermediate strap portion are oriented to avoid contact with the patient's ears in use, wherein the upper strap portion is constructed and arranged to engage a portion of the patient's parietal bones in use to resist downward movement of the headgear assembly, wherein the cross-bar strap portion is structured to engage a portion of the patient's occipital bone in use and the rear lower strap portion is structured to engage a rear upper portion of the patient's neck to resist upward movement of the headgear assembly in use, wherein the cross-bar strap portion, the first upper intermediate strap portion, the second upper intermediate strap portion, and the upper strap portion define an upper opening therebetween, wherein the cross-bar strap, the first lower intermediate strap portion, the second lower intermediate strap portion, and the rear lower strap portion define a lower opening therebetween, wherein the headgear assembly is constructed from a composite material comprising a first layer of material configured to be positioned against the patient's head in use and a second layer of material further comprising a loop material, and wherein the lower opening and the upper opening are dimensioned such that the upper opening is configured to accommodate a larger portion of the patient's head in use than the lower opening.

18. The respiratory mask assembly according to claim 17, further comprising a strip of hook material attached to the composite material adjacent to a free end of each upper side strap portion and each lower side strap portion for attachment to the loop material, the strip of hook material and the loop material configured to form a hook-and-loop connection.

19. The respiratory mask assembly according to claim 17, wherein one of the first layer of material and the second layer of material has a more rigid construction than the other of the first layer of material and the second layer of material to resist compression of the rear lower strap portion in a superior direction in use and thereby resist movement of each lower side strap portion in the superior direction.

20. The respiratory mask assembly according to claim 17, wherein the upper strap portion is configured to extend across an upper portion of the patient's head.

21. The respiratory mask assembly according to claim 17, wherein the rear lower strap portion is configured to extend across a lower, rear portion of the patient's neck in use, and the cross-bar strap portion is configured to extend across a lower, rear portion of the patient's head in use.

22. The respiratory mask assembly according to claim 17, wherein the upper opening and the lower opening are oriented on the patient in use such that the upper opening and the lower opening are substantially bisected by the patient's median plane.

23. The respiratory mask assembly according to claim 17, wherein the cross-bar strap portion, the first lower intermediate strap portion, the second lower intermediate strap portion, the first upper intermediate strap portion, and the second upper intermediate strap portion are configured to engage the patient's head behind the patient's ears in use.

24. The respiratory mask assembly according to claim 17, wherein a lowermost edge of the rear lower strap portion is configured to be positioned superior to a lowermost edge of each of the lower side strap portions on the patient's head in use.

25. The respiratory mask assembly according to claim 17, wherein the headgear assembly further comprises a strip of hook material attached to the composite material adjacent to a free end of each upper side strap portion and each lower side strap portion for attachment to the loop material, the strip of hook material and the loop material forming a hook-and-loop connection,
wherein the upper strap portion is configured to extend across the rear upper portion of the patient's head,
wherein the cross-bar strap portion, the first lower intermediate strap portion, the second lower intermediate strap portion, the first upper intermediate strap portion, and the second upper intermediate strap portion are configured to engage the patient's head behind the patient's ears in use,
wherein a lowermost edge of the rear lower strap portion is configured to be positioned superior to a lowermost edge of each of the lower side strap portions on the patient's head in use,
wherein the cross-bar strap portion is wider than the rear lower strap portion, and
wherein the rear lower strap portion is configured to extend across a lower, rear portion of the patient's neck in use, and the cross-bar strap portion is configured to extend across a lower, rear portion of the patient's head in use.

26. The respiratory mask assembly according to claim 17, wherein each upper side strap portion is configured to be attached to the forehead support and each lower side strap portion is configured to be attached to the mask frame.

27. The respiratory mask assembly according to claim 26, further comprising a clip structure configured to attach each lower side strap portion to the mask frame, wherein each lower side strap portion is configured to be wrapped around a corresponding clip structure.

28. The respiratory mask assembly according to claim 26, wherein each upper side strap portion is configured to be attached to the forehead support.

29. The respiratory mask assembly according to claim 17, wherein the cross-bar strap portion is wider than the rear lower strap portion.

* * * * *